US011376991B2

(12) United States Patent
Oommen et al.

(10) Patent No.: US 11,376,991 B2
(45) Date of Patent: Jul. 5, 2022

(54) AUTOMOBILE SEAT WITH USER PROXIMITY TRACKING

(71) Applicant: Bose Corporation, Framingham, MA (US)

(72) Inventors: Binu Oommen, Franklin, MA (US); Muhammad Haris Usmani, Waltham, MA (US); Bradford Kyle Subat, Northborough, MA (US); John Leslie Benton, Northbridge, MA (US); Charles Terence Henry Oswald, Salem, NY (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 16/916,308

(22) Filed: Jun. 30, 2020

(65) Prior Publication Data

US 2021/0402891 A1 Dec. 30, 2021

(51) Int. Cl.
| | |
|---|---|
| *B60N 2/879* | (2018.01) |
| *B60N 2/00* | (2006.01) |
| *B60N 2/809* | (2018.01) |
| *A61B 5/00* | (2006.01) |
| *B60N 2/58* | (2006.01) |
| *B60N 2/64* | (2006.01) |
| *B60N 2/80* | (2018.01) |

(52) U.S. Cl.
CPC ............ *B60N 2/002* (2013.01); *A61B 5/6893* (2013.01); *B60N 2/58* (2013.01); *B60N 2/64* (2013.01); *B60N 2/809* (2018.02); *B60N 2/879* (2018.02); *B60N 2002/899* (2018.02)

(58) Field of Classification Search
CPC ........ B60N 2/002; B60N 2/879; B60N 2/809; B60N 2/58; B60N 2/64; B60N 2002/899; A61B 5/6893
See application file for complete search history.

(56) References Cited

U.S. PATENT DOCUMENTS

| | | | | |
|---|---|---|---|---|
| 7,640,090 B2* | 12/2009 | Uchida | ................... | B60N 2/002 701/49 |
| 7,963,598 B2* | 6/2011 | Akaike | ................... | B60N 2/888 297/216.12 |

(Continued)

FOREIGN PATENT DOCUMENTS

| | | |
|---|---|---|
| DE | 102015222715 A1 | 5/2017 |
| FR | 3098769 * | 7/2019 |
| WO | 2019029854 A1 | 2/2019 |

OTHER PUBLICATIONS

Machine translation of FR3098769 (Year: 2019).*

(Continued)

*Primary Examiner* — Philip F Gabler
(74) *Attorney, Agent, or Firm* — Hoffman Warnick LLC (57) ABSTRACT

Various implementations include seats and related systems for detecting user proximity and controlling one or more functions based on that proximity detection. In particular cases, the seats include capacitive sensors for detecting user proximity. In some particular aspects, an automobile seat includes: a core section; a cover over at least a portion of the core section, the cover having a set of capacitive sensors across a front of the seat; and a processor for processing signals from the set of capacitive sensors to detect a proximity of a user.

20 Claims, 5 Drawing Sheets

(56) References Cited

U.S. PATENT DOCUMENTS

| | | | | |
|---|---|---|---|---|
| 9,191,997 | B2* | 11/2015 | Weiss | H05B 3/342 |
| 10,233,571 | B1* | 3/2019 | Alexander | D03D 1/0088 |
| 10,313,819 | B1* | 6/2019 | Dublin | H04R 5/04 |
| 10,457,179 | B1 | 10/2019 | Kentley-Klay | |
| 2006/0164254 | A1* | 7/2006 | Kamizono | B60R 21/01532 |
| | | | | 340/667 |
| 2015/0158494 | A1* | 6/2015 | Lee | B60W 40/08 |
| | | | | 324/671 |
| 2018/0037137 | A1* | 2/2018 | Goedert | G01R 27/26 |
| 2018/0178676 | A1* | 6/2018 | Cech | B60W 30/00 |
| 2019/0174226 | A1* | 6/2019 | Yang | G10L 15/28 |
| 2019/0176670 | A1 | 6/2019 | Scott et al. | |
| 2019/0390982 | A1 | 12/2019 | Oel | |
| 2020/0171979 | A1* | 6/2020 | Yetukuri | B60N 2/002 |
| 2020/0377015 | A1* | 12/2020 | Yamamoto | B60N 2/002 |
| 2021/0016683 | A1* | 1/2021 | Balde | B60N 2/64 |

OTHER PUBLICATIONS

PCT International Search Report and Written Opinion for International Application No. PCT/US2021/038223, dated Sep. 22, 2021, 15 pages.

\* cited by examiner

AUTOMOBILE SEAT WITH USER PROXIMITY TRACKING

TECHNICAL FIELD

This disclosure generally relates to seats and sensors. More particularly, the disclosure relates to seats with integrated sensors for detecting user proximity.

BACKGROUND

Conventional seating arrangements, for example, in automobiles, focus on user support and comfort. In some cases, these seating arrangements integrate speakers for providing audio output. However, these conventional seating arrangements fail to capitalize on detectable user characteristics that can aid in system controls.

SUMMARY

All examples and features mentioned below can be combined in any technically possible way.

Various implementations include seats and related systems for detecting user proximity and controlling one or more functions based on that proximity detection. In particular cases, the seats include capacitive sensors for detecting user proximity.

In some particular aspects, an automobile seat includes: a core section; a cover over at least a portion of the core section, the cover having a set of capacitive sensors across a front of the seat; and a processor for processing signals from the set of capacitive sensors to detect a proximity of a user.

In additional particular aspects, a system includes: an automobile seat including: a core section; a cover over at least a portion of the core section, the cover having a set of capacitive sensors across a front of the seat for detecting a head position of a user; and a processor coupled with the set of capacitive sensors for detecting a proximity of a user.

In further aspects, a seat includes: a core section; a cover over at least a portion of the core section, the cover having a set of capacitive sensors across a front of the seat; and a processor for processing signals from the set of capacitive sensors to detect a proximity of a user.

In additional aspects, a seat includes: a core section comprising at least one pad; a cover over at least a portion of the core section; a set of capacitive sensors across a front of the seat between the core section and the cover; and a processor for processing signals from the set of capacitive sensors to detect a proximity of a user.

Implementations may include one of the following features, or any combination thereof.

In certain aspects, the set of capacitive sensors are arranged in a matrix across the front of the seat.

In particular cases, the matrix of capacitive sensors are located in a headrest portion of the seat or in a backrest portion of the seat.

In some implementations, the matrix of capacitive sensors are distributed on both sides of a vertical centerline of the front of the seat, and the processor is configured to detect side-to-side (e.g., horizontal) movement of the user based on signals from the matrix of capacitive sensors.

In certain aspects, the matrix of capacitive sensors are distributed on both sides of a horizontal centerline of the front of the seat, and the processor is configured to detect vertical movement of the user based on signals from the matrix of capacitive sensors.

In certain aspects, the processor is configured to determine at least one of a position of the user or a movement of the user based on the detected proximity to the set of capacitive sensors.

In particular implementations, the matrix of capacitive sensors includes at least four zones, with at least two zones located on each side of a vertical centerline of the seat.

In some cases, zones on a same side of the vertical centerline are configured to detect vertical movement of the head of the user.

In certain implementations, the matrix of capacitive sensors includes at least six zones, with at least three zones located on each side of the vertical centerline.

In particular cases, the set of capacitive sensors is configured to detect at least one of: a leaning movement of the user, side-to-side movement of the user, shifting movement of the user, or movement between a seated position and an unseated position.

In certain aspects, the automobile seat further includes a controller coupled with the processor, where the controller is configured to control functions in the automobile based on the detected proximity of the user.

In some cases, the controller is configured to enable gesture-based controls, for example, as detected using the capacitive sensors.

In particular implementations, the functions in the automobile include at least one of: an audio playback setting in the automobile, microphone functionality in the automobile, a navigation function for a navigation system, a phone setting for a paired phone or a height setting for the automobile seat.

In certain cases, the audio playback setting includes at least one of: volume, left/right channel selection, center image adjustment, or playback selection (e.g., track selection or station selection).

In some cases, the microphone functionality includes beamforming, for example, to enhance voice capture.

In particular aspects, the height setting includes a height of the seat, for example, in the automobile, or a height of a headrest in the seat.

In certain implementations, the processor is located in the core section and is physically separated from the controller or is located proximate the controller in a control section of the automobile.

In some cases, the controller is configured to control output of at least one audio prompt requesting user feedback that is detectable with a change in a head position of the user, and wherein the controller is configured to process the user feedback as a change in the head position of the user only for a designated period following output of the at least one audio prompt.

In particular aspects, the controller is further configured to process the signals from the capacitive sensors to detect at least one health indicator of the user. In certain cases, the health indicator includes respiration rate, drowsiness and/or alertness.

In certain cases, the controller is further configured to process signals from an additional detection system, and the controller is configured to verify the signals from the additional detection system with the signals from the set of capacitive sensors.

In some implementations, the additional detection system includes at least one of: a motion detection system, a position detection system or an orientation detection system. In particular cases, the additional detection system includes a two-dimensional (2D) camera, a three-dimensional (3D) cameras, an optical sensor, an inertial measurement unit (IMU), and/or an acoustic-based sensor such as a microphone or array of microphones.

In some cases, the core includes a skeletal support structure, the cover includes a fabric, and the set of capacitive sensors are embedded within the fabric or woven into the fabric.

In certain aspects, the system further includes a transducer coupled with the controller, where the controller is configured to: initiate output of at least one audio prompt via the transducer, the at least one audio prompt requesting user feedback that is detectable with a change in the proximity of the user to at least one of the set of capacitive sensors; and process the user feedback as a change in the proximity of the user to the at least one capacitive sensor only for a designated period following output of the at least one audio prompt.

Two or more features described in this disclosure, including those described in this summary section, may be combined to form implementations not specifically described herein.

The details of one or more implementations are set forth in the accompanying drawings and the description below. Other features, objects and benefits will be apparent from the description and drawings, and from the claims.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

This disclosure is based, at least in part, on the realization that a capacitive-based sensor system can be beneficially deployed in a seat, such as an automobile seat, to control one or more functions. For example, an automobile seat can include a set of capacitive sensors for detecting user presence and/or position/movement in order to control functions in the automobile. In some cases, the set of capacitive sensors function as an interface for the user with the controller in the automobile. When compared with conventional approaches, the seats and systems disclosed herein enable enhanced control of automobile functions, as well as a gesture-based or movement-based interface for users.

Commonly labeled components in the FIGURES are considered to be substantially equivalent components for the purposes of illustration, and redundant discussion of those components is omitted for clarity.

Figure 1:
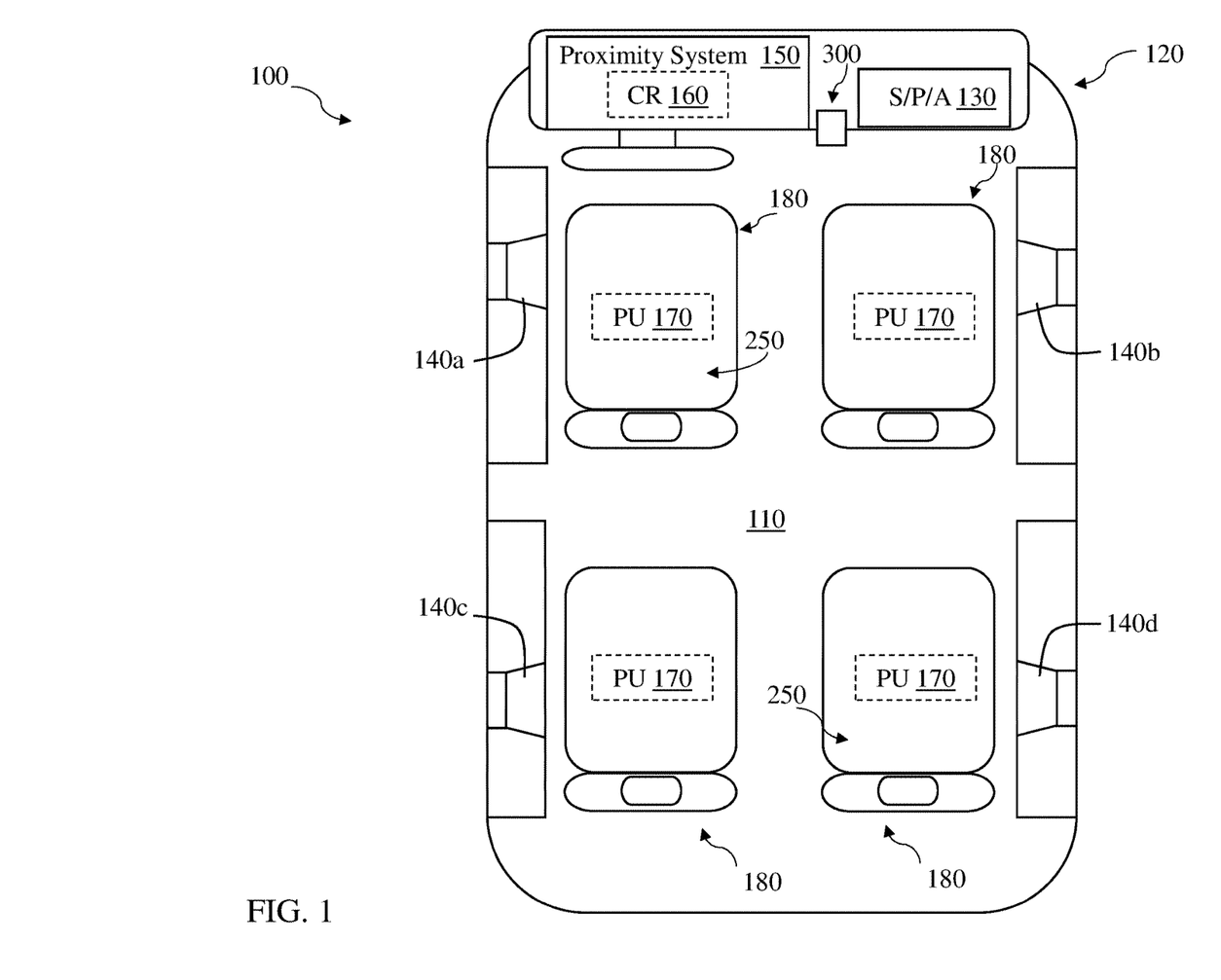
FIG. 1 is a schematic top cut-away view of an example environment according to various implementations.

FIG. 1 is a schematic illustration of an environment 100 according to various implementations. In some cases, the environment 100 includes the cabin of a vehicle, such as an automobile. However, in other cases, the environment 100 can include an airplane cabin, a home theater or gaming room, an amusement park ride, etc. The example environment 100 shown in FIG. 1 depicts a vehicle having an audio system with a speaker on each of the four doors. It is understood that this configuration is only one example of an automobile (and associated audio system) used to illustrate various implementations of the disclosure, and that a variety of additional configurations can be utilized with these implementations.

As shown, the environment 100 can include a cabin 110 (e.g., automobile or other cabin), along with an audio system 120. The audio system 120 is shown including a combined source/processing/amplifying unit (S/P/A) 130 and a set of speakers 140a-d. In some examples, the different functions of the combined source/processing/amplification unit 130 may be divided between multiple components. In particular, the source is often separated from the amplifier, and the processing is provided by either the source or the amplifier, though the processing may also be provided by a separate component. The processing may also be provided by software loaded onto a general purpose computer providing functions of the source and/or the amplifier. We refer to signal processing and amplification provided by "the system" generally, without specifying any particular system architecture or technology. In this example, fixed speakers 140a-b are shown, which can include at least one high, or mid-to-high range speaker element (e.g., tweeter) and at least one low, or low-to-mid range speaker element (e.g., woofer). Additional description of the audio system 120 and variations on its configuration are included in U.S. Pat. No. 10,313,819 (Phantom Center Image Control), which is incorporated by reference in its entirety.

Also shown in the environment 100 is a proximity-based control system (or "proximity system") 150. In certain implementations, the proximity system 150 utilizes or includes one or more components in the audio system 120 to perform functions described herein. In some cases, the proximity system 150 is executed as software (e.g., a software module) in a common processing component with other components in the audio system 120. In certain cases, the proximity system 150 includes a controller (CR) 160 for performing one or more functions described herein. In some aspects, the controller 160 includes a control circuit and/or one or more processors (PU) for performing functions described herein. As described herein, in certain cases, the proximity system 150 also includes a processor (PU) 170 that is physically separated from the controller 160, e.g., in or proximate a seat 180 in the cabin 110. In certain cases, the processor 170 is configured to communicate with the controller 160, e.g., via any conventional hard-wired and/or wireless means. According to some additional implementations, the processor 170 is physically proximate the controller 160, or is integral with the controller 160, such as where the processor 170 is located with the controller 160 in a centralized control system (e.g., an automobile control system or aviation control system).

Figure 2:
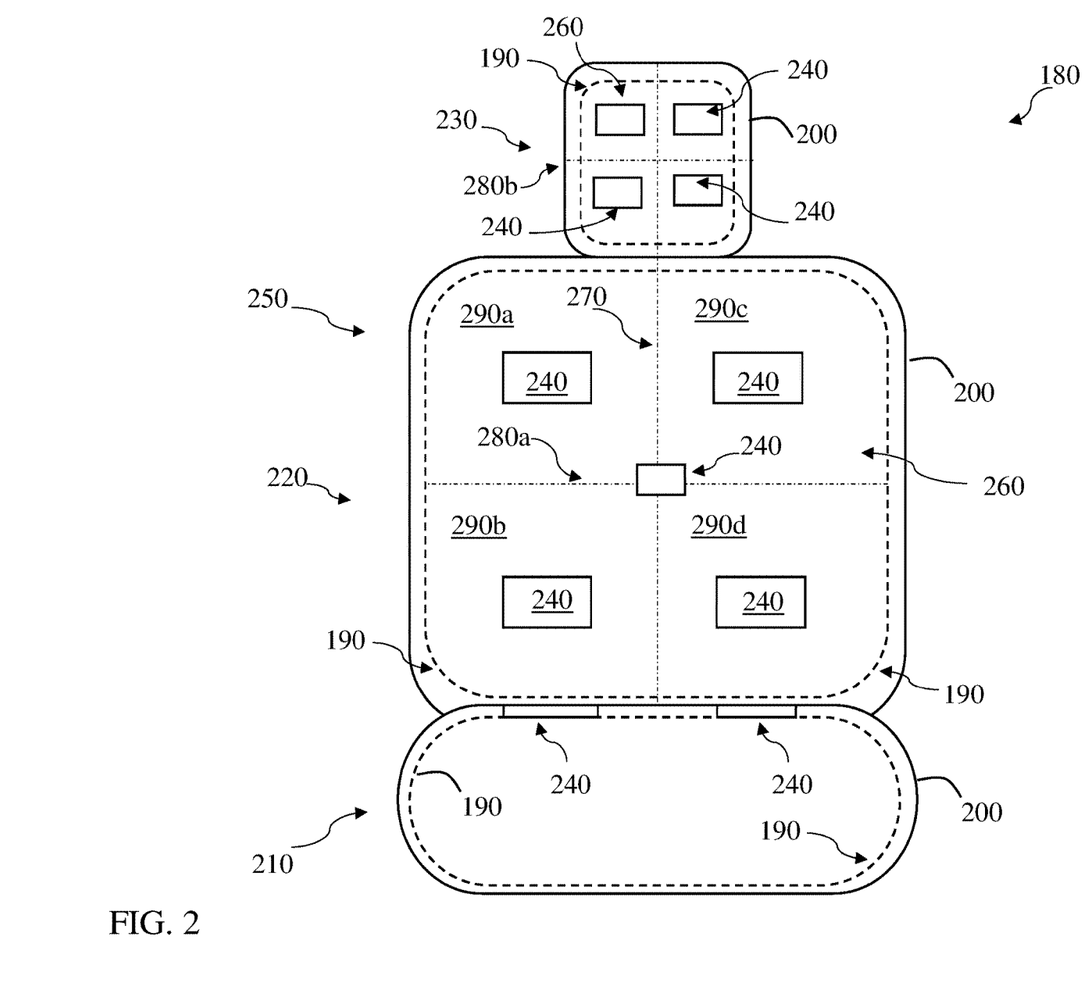
FIG. 2 is a front view of a seat in the environment of FIG. 1, according to various implementations.
Figure 3:
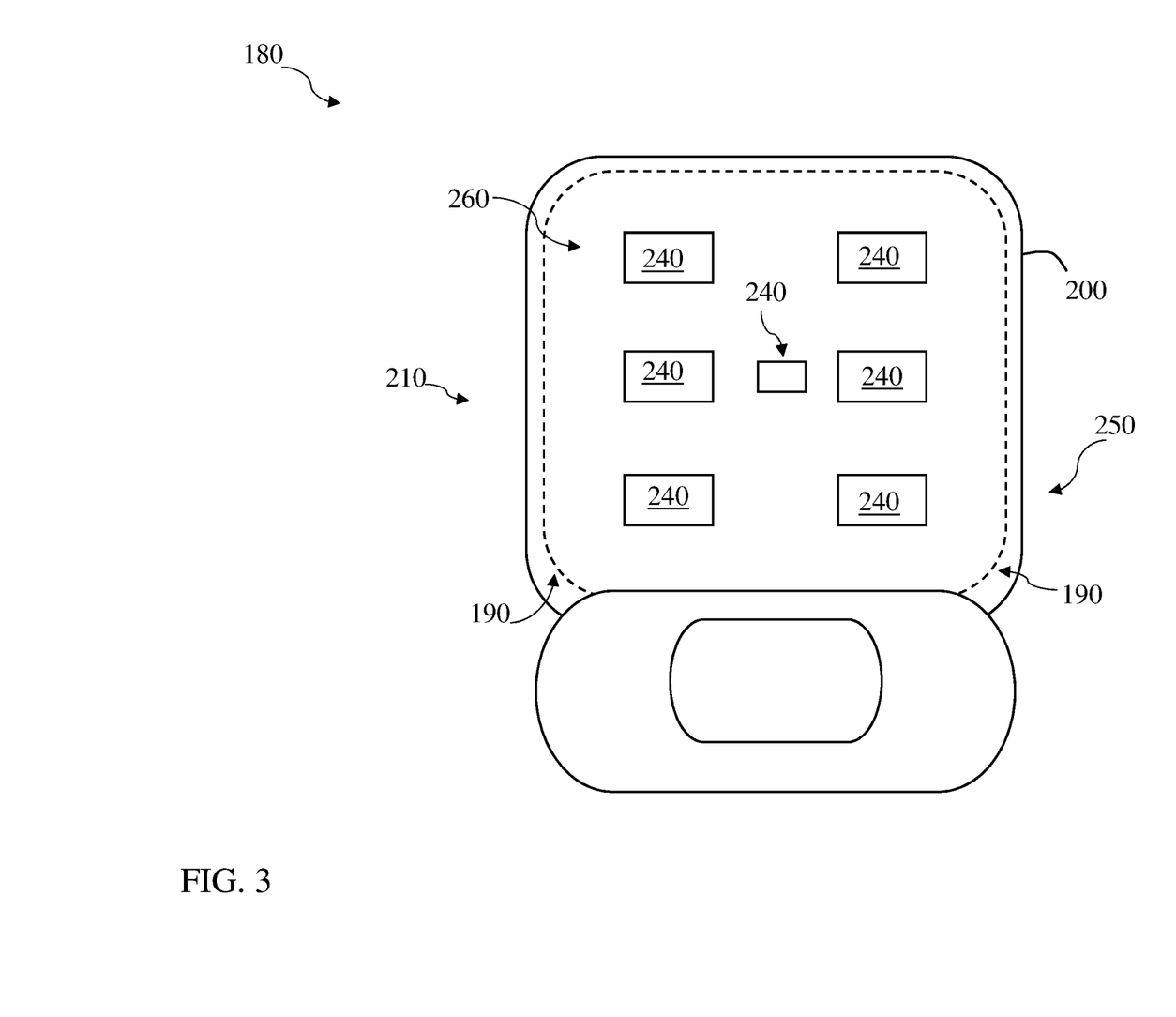
FIG. 3 is a top view of a seat in the environment of FIG. 1, according to various implementations.

FIG. 2 shows a close-up front view of a portion of a seat 180 in the cabin 110 of FIG. 1, and FIG. 3 shows a top view of the portion of the seat 180 in FIG. 2. FIGS. 1-3 are referred to simultaneously. It is understood that seat 180 can include any of the seats illustrated in the cabin 110, such that one or more of the seats can include features described with respect to seat 180 in FIGS. 2 and 3. According to various implementations, one or more seats 180 in the cabin 110 can include a core section 190, and a cover 200 over at least a portion of the core section 190. The core section 190 is illustrated in phantom, and can include structural support elements of the seat 180, e.g., a skeletal support structure and associated padding and adjustment mechanisms for positioning. In certain cases, the seat 180 includes a base 210, a backrest 220 and a headrest 230. In other cases, the seat 180 includes only a base 210, or only a base 210 and a backrest 220. In particular implementations, the base 210, backrest 220 and/or headrest 230 are integral with one another, such that they are formed as a single component. In various implementations, the cover 200 includes a fabric or other protective material, e.g., cloth, canvas, leather, or synthetic. As used herein, in various implementations, the general term "seat" can refer collectively to a base 210, backrest 220 and headrest 230. That is, in certain implementations, the proximity system 150 is configured to detect user proximity, position, orientation, and/or movement with sensors at one or more portions of the seat 180. It is understood that reference to the seat 180 can include reference to one or more sections of the seat 180.

In particular cases, the cover 200 also includes a set of capacitive sensors 240 located across the front 250 of the seat 180. In some examples, such as where the cover 200 includes a fabric, the set of capacitive sensors (or, sensors) 240 are embedded within the fabric or woven into the fabric. However, the sensors 240 can be coupled, affixed or otherwise joined with the cover 200 using any of a variety of additional approaches. In additional implementations, the sensors 240 are located between the core section 190 and the cover 200, e.g., mounted to the backside of the cover 200, a padding section in the core 190 and/or another support structure within the core section 190. In some cases, the sensors 240 are positioned on a support structure such as a mount or plate beneath the cover 200 and/or integrated into the cover 200. As noted herein, in certain cases, the set of capacitive sensors 240 can include at least one capacitive sensor 240. In various additional implementations, the set of capacitive sensors includes two or more capacitive sensors 240. The capacitive sensors 240 are coupled with the processor 170 (FIG. 1), which can be located at or near the seat 180 and/or at or near the controller 160 (e.g., in a centralized control module). In certain cases, the capacitive sensors 240 are configured to detect the proximity of a user, e.g., a human user, to the seat 180. According to particular implementations, the capacitive sensors 240 detect a change in capacitance when they come in contact with a user's body (e.g., a user's head, back, neck, legs, etc.). The processor 170 receives signals from the capacitive sensors 240 indicative of these changes in capacitance, and processes those signals to detect user proximity.

In certain cases, as illustrated in one example in FIG. 2, the capacitive sensors 240 are arranged in a matrix 260 (e.g., a 2×2, 3×3, 3×2, 2×3, 4×2, 2×4, etc. matrix) across the front 250 of the seat 180. In some implementations, one or more matrices 260 can be located on different sections of the seat 180, and may function independently, or a plurality of sensors 240 can be arranged in a matrix 260 that spans between different sections of the seat 180, e.g., with sensors 240 on the backrest 220 and/or the headrest 230.

Figure 4:
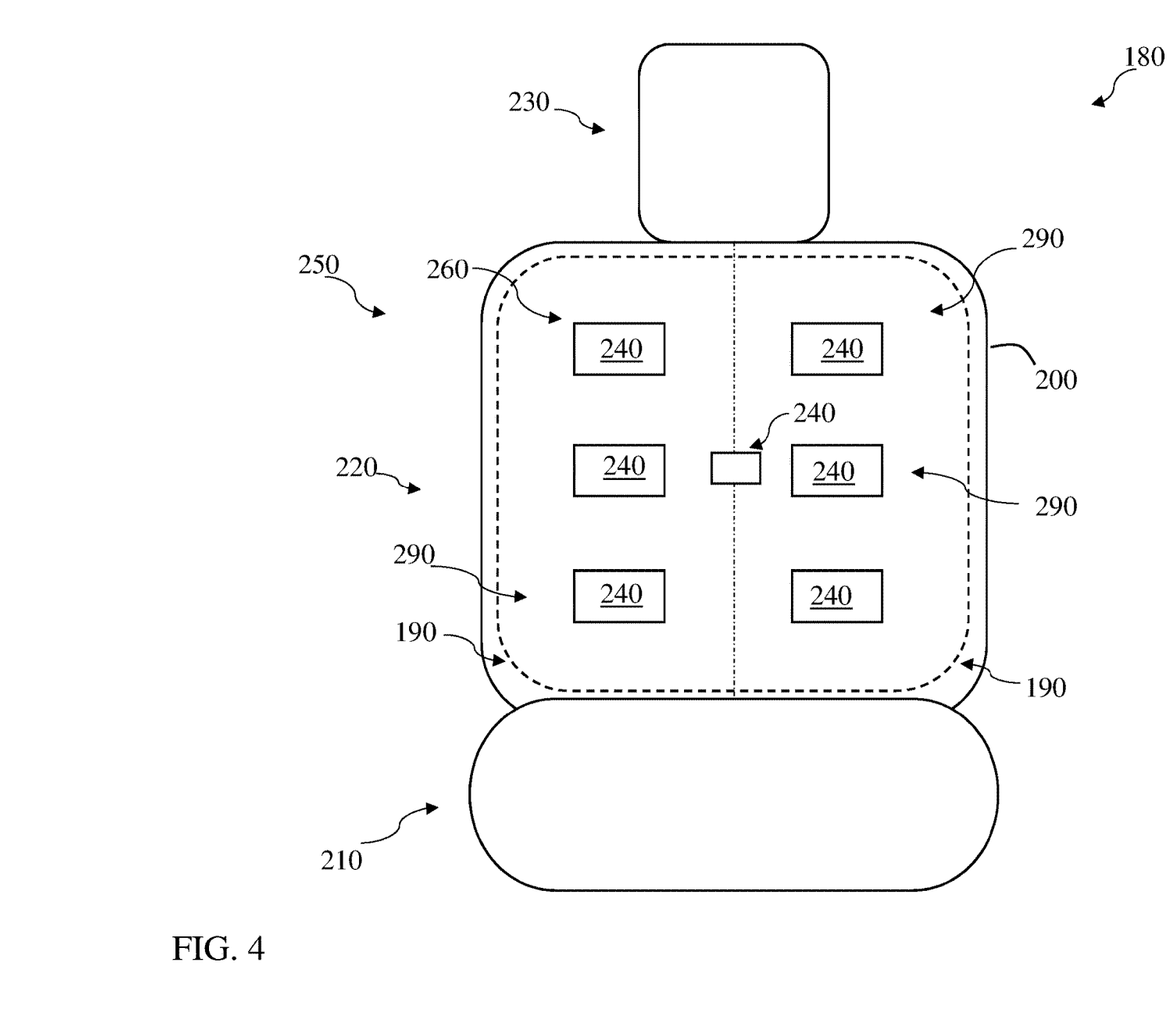
FIG. 4 illustrates a configuration of sensors in a seatback according to various implementations.

As illustrated in FIG. 2, according to some implementations, the matrix 260 includes sensors 240 that are distributed on both sides of a vertical centerline 270 of the front 250 of the seat 180 (e.g., a front of the backrest 220 and/or the headrest 230). In some examples, one or more sensors 240 are located on each side of the vertical centerline 270. In these implementations, the processor 170 is configured to detect side-to-side (e.g., horizontal) movement of a user based on signals from the sensors 240, e.g., as a relative capacitance changes on the left sensor 240 versus right sensor 240. In certain additional or alternative configurations, the matrix 260 includes sensors 240 that are distributed on both sides of a horizontal centerline 280 of the front of the seat 250 (e.g., a front of the backrest 220 and or the headrest 230, with two distinct horizontal centerlines 280*a*, 280*b* shown for the backrest 220 and headrest 230, respectively). In these implementations, the processor 170 is configured to detect vertical movement of a user based on signals from the sensors 240, e.g., as a relative capacitance changes on the lower sensor 240 versus upper sensor 240. In some examples, two or more sensors 240 are located on each side of the vertical centerline 270. In these cases, as illustrated in the example configuration in backrest 220, two zones 290*a,b* are located on one side of the vertical centerline 270, while two zones 290*c,d* are located on the other side of the vertical centerline 270. In some cases, zones (e.g., 290*a,b*) are distributed on opposite sides of the horizontal centerline 280 as well. In any case, zones on the same side of the vertical centerline 270 (e.g., zones 290*a,b*) are configured to detect vertical movement of the user, e.g., leaning forward or backward in the case that the matrix 260 is located on the backrest 220, or forward/backward or vertical movement of the head of the user in the case that the matrix 260 is located on the headrest 230. In some particular examples, as illustrated in FIG. 4, the matrix 260 can include at least six (6) zones 290, with three zones located on each side of the vertical centerline 270. It is understood that the illustrations of matrices are not limiting of the various aspects of the disclosure. For example, one or more sensors 240 can be located on a centerline (e.g., vertical centerline 270 and/or horizontal centerline 280) in addition to, or alternatively to, the sensors 240 shown in matrix 260 or any other matrices shown or described herein. FIGS. 2-5 illustrate examples of additional sensors 240 shown approximately on or near one or more centerlines in a particular section of the seat 180.

Figure 5:
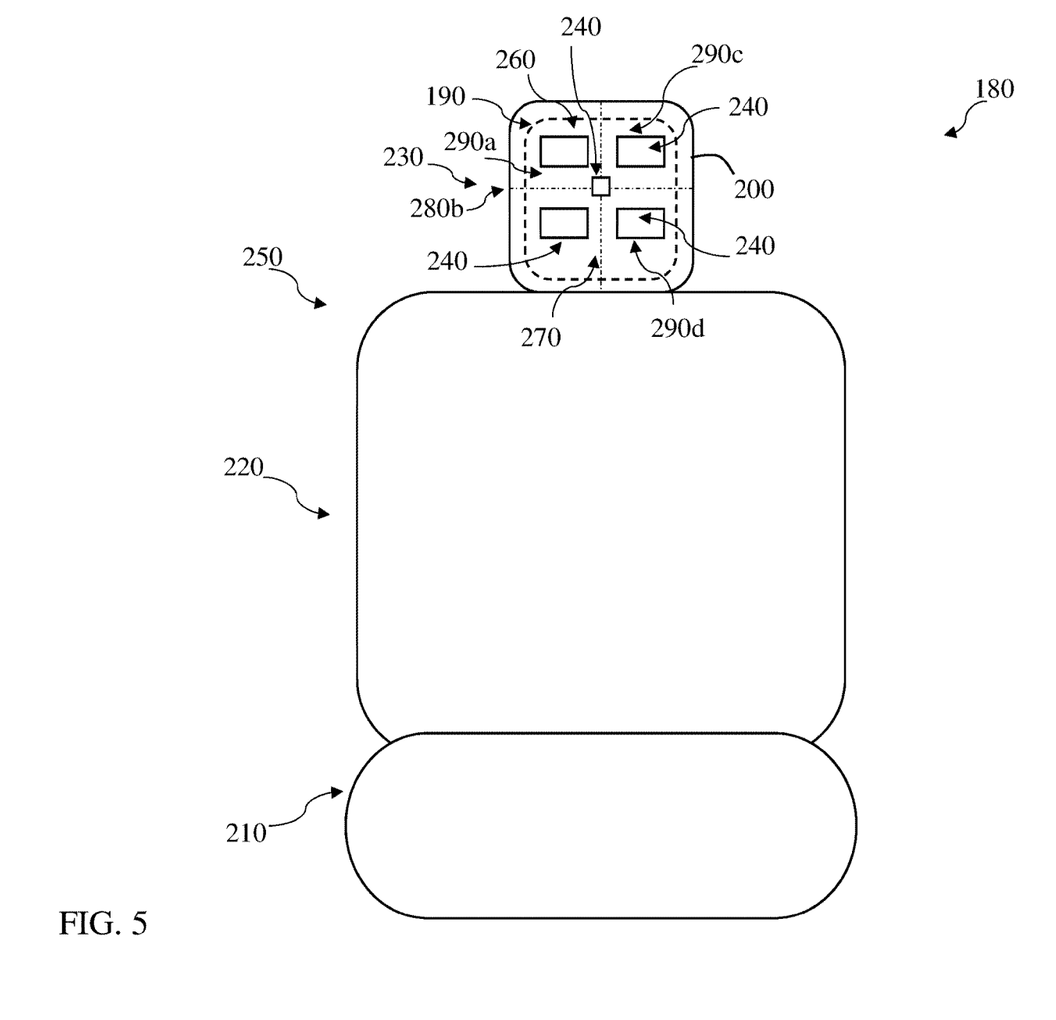
FIG. 5 illustrates a configuration of sensors in a headrest according to various implementations.

In particular examples, a matrix 260 of sensors 240 is shown across the backrest 220 in FIG. 4, while a matrix 260 of sensors is shown across the headrest 230 in FIG. 5. In these implementations, each matrix 260 of sensors 240 can be configured to detect proximity of different portions of the user's body, e.g., proximity of the user's head, back, legs/seat, etc. In some implementations, as noted herein, the sensors 240 are configured to detect user movement and/or position, as well as proximity. That is, the sensors 240 in distinct zones 290 send signals to the processor 170 indicating proximity, or changes in proximity, of the user to the sensors 240 in those zones 290. In certain cases, the sensors 240 can indicate whether a user is in a seated position or in an unseated position, as well as indicating transitions (i.e., movement) between those positions. For example, the sensors 240 in the backrest 220 can indicate whether a user's back is proximate the backrest 220, while sensors 240 in the headrest 230 can indicate whether the user's head is proximate the headrest 230. Sensors 240 in the base 210 can indicate whether the user is in the seat 180. In additional examples, sensors 240 in the backrest 220 and/or headrest 230 can indicate whether the user is leaning, e.g., leaning forward or backward, and/or left or right. In these cases, when sensors 240 on both sides of the vertical centerline 270 indicate a change in proximity, it is likely that the user is either leaning forward (change from near to far) or leaning back (change from far to near). Sensors 240 in vertically arranged zones 290 can also detect leaning, e.g., where a lower zone 290 has sensors 240 that indicate proximity to the user while an upper zone 290 has sensors 240 that indicate the user is not proximate. In some cases, these zones are located on different sides of the horizontal center line 280, but in other cases, these zones can be near one another and/or border one another. In other examples, when sensors 240 on only one side of the vertical centerline 270 detect proximity, this can be indicative of side-to-side movement by the user or shifting movement by the user.

Returning to FIG. 1, as noted herein, the controller 160 is configured to control functions in the cabin 110 based on the detected proximity of the user to one or more sensors 240. In the example of an automobile, the controller 160 is configured to control automobile functions based on the detected proximity of the user to one or more sensors 240. In particular examples, the controller 160 is configured to enable gesture-based control of functions in the cabin 110 using sensors 240.

In the automobile control example, the controller 160 is configured (i.e., programmed) to control functions in the automobile including at least one of: an audio playback setting in the automobile, microphone functionality in the automobile, a navigation function for a navigation system, a phone setting for a paired phone or a height setting for the automobile seat. Audio playback settings can define playback via the audio system 120 and/or another connected audio system such as a portable audio device or wearable audio device. Audio playback settings can include audio signal filters, volume, left versus right channel input, center image location, playback or streaming selection, track or station, etc. In certain cases, the controller 160 enables adjustment of audio playback settings with changes in detected user proximity. In particular cases, these settings can be adjusted with a gesture detected by sensors 240, e.g., a head nod or a head shake detected by sensors 240 in the headrest 230. In additional cases, these settings are adjusted based on detected changes in the user position, e.g., such that left/right channel inputs or center image are adjusted in response to detecting that the user shifts or leans in the seat 180.

In particular examples, audio signal filters to transducers 140 (e.g., in the doors, dash, overhead and/or in the headrests) are controlled based on a detected position or movement by the user. In certain examples, the controller 160 is configured to adjust audio signal filters to headrest transducers based on detected movement by the user within the seat 180. In one example, the controller 160 adjusts the center image of the audio output from transducers 140 (e.g., in headrest and/or other sections of cabin 110) in response to detecting that the user leans left or right. In particular cases, the controller 160 is configured to adjust the audio signal filters to transducers in the headrest to adjust the center image when detecting that the user's head has moved relative to those transducers, e.g., to maintain a stable center image despite user head movement. This can be accomplished by modifying the magnitude and phase of signals sent to the headrest transducers. In other examples, the controller 160 is configured to adjust the frequency-based output level at the transducers 140 (e.g., in headrest and/or other sections of cabin 110) as the user leans forward or otherwise leans away from the headrest.

Microphone functionality, which is controlled by certain detected changes in user proximity, can include adjusting beamforming coefficients or beamforming techniques to enhance user voice pickup. In some implementations, the controller 160 is configured to receive an indicator (e.g., from processor 170) that the user's head position changed (e.g., as indicated by relative proximity change between sensors 240 in left and right zones 290), and adjust the microphone functionality to enhance voice pickup from a different direction. In certain additional cases, the controller 160 can enable or disable voice commands in response to detecting the user's position change, e.g., enabling commands when the user looks forward and disabling commands when the user looks down or to the side. In additional examples, the controller 160 is configured to adjust beamforming coefficients to enhance microphone pickup based on positional estimates or indicators, e.g., seat 180 locations and/or movement of the user within the seat 180. In certain examples, the controller 160 uses detected seat location information as well as relative movement information about the user to calculate beamforming coefficients to enhance voice pickup at the microphones.

In certain other examples, the controller 160 is configured to adjust a height setting for the seat 180 in response to detecting proximity, e.g., by adjusting the headrest 230 height relative to the backrest 220 in response to detecting that the user is sitting low or high in the seat 180. In example cases, an upper zone 290 of sensors 240 may not indicate proximity while a lower zone 290 of sensors 240 indicates proximity, and the controller 160 can infer that the user is sitting below the detectable height for the upper zone of sensors 290. In these cases, the controller 160 is configured to lower the height of the headrest 230 relative to the backrest 220 to more fully support the user's head. The controller 160 can perform similar functions to raise the height of the headrest 230, for example, in response to detecting that a lower zone 290 of sensors 240 does not indicate proximity while an upper zone of sensors 290 does indicate proximity, the controller is configured to raise the headrest 230 relative to the backrest 220. Additionally, the controller 160 can perform similar functions to tilt the headrest 230 forward or backward in response to detecting user proximity, e.g., to improve safety by placing closer to the user's head and/or to improve audio performance by placing the headrest 230 closer to or farther from the user's head for particular audio outputs.

In certain cases, the controller 160 is configured to control output of at least one audio prompt requesting user feedback that is detectable with a change in the user's head position. For example, the controller 160 is configured to initiate output (e.g., via speakers 140), of an audio prompt that requests feedback in the form of a user head gesture such as a head nod, head shake, quick turn or look, etc. In particular implementations, the controller 160 is configured to remain in a query mode only for a designated period after initiating the audio prompt. That is, the response to the audio prompt must be detected within the query period to register with the controller 160 (and trigger the subsequent action). In these cases, the controller 160 allows users to ignore prompts and/or avoid falsely triggering a response with a head gesture, which may enhance hands-free control of one or more functions in the cabin 110.

In still further implementations, the controller 160 is configured to process signals from the sensors 240 to detect one or more health indicators of the user. For example, in certain implementations, capacitive sensors 240 in the backrest 220 are positioned to detect user respiration (e.g., respiration rate). In these examples, the sensors 240 are positioned to sense the user's movement associated with alternating inhalation and exhalation. In certain implementations, the controller 160 is configured to take action in response to detecting that the user's respiration rate deviates from a threshold, e.g., a personalized respiration rate range defined by the user or learned over time (e.g., using a machine learning component), or a generally accepted range of respiration rates for a healthy individual. In some cases, the controller 160 is configured to provide an alert to the user or to a third party (e.g., medical personnel or an emergency response unit) in response to detecting that the user's respiration rate deviates from the threshold for a period (e.g., a statistically significant period). In certain implementations, the controller 160 is configured to process signals from the sensors 240 to detect additional health indicators such as: drowsiness (sleepiness) or alertness. For example, in certain cases the controller 160 is configured to detect that the user is drowsy/sleepy, and based on the user's seat location, initiate one or more actions. In response to detecting that the driving user is drowsy or otherwise not alert, the controller 160 is configured to adjust cabin lights (e.g., brighter), volume of audio playback (e.g., louder), and/or provide an alert or other stimulant such as an audible alert or vibrotactile alert via the seat and/or the steering wheel. In response to detecting that a passenger user is drowsy, the controller 160 is configured to adjust cabin lights (e.g., dimmer), volume of audio playback (e.g., softer), etc. to enhance sleeping conditions for that passenger user. In particular cases, the controller 160 is configured to adjust one or more parameters (e.g., lighting, audio playback, stimulation) on a row-by-row, seat-by-seat and/or sector-by-sector basis.

In still further implementations, the controller 160 is configured to process signals from an additional detection system to enable one or more control functions. For example, as shown in FIG. 1, the controller 160 can be connected with an additional detection system 300 that is configured to detect one or more aspects of user motion and/or gesture(s). In certain cases, the additional detection system 300 is configured to detect user motion, position and/or change in position, and/or orientation and/or change in orientation, and provide corresponding data to the controller 160. Examples of additional detection systems 300 include one or more two-dimensional or three-dimensional optical sensors (e.g., camera), one or more inertial measurement units (IMUs), an acoustic-based sensor (e.g., one or more microphones or a microphone array), etc. In particular cases, the additional detection system 300 can be referred to as a head and/or body orientation and/or position detection system. In certain implementations, the controller 160 is configured to verify the signals from the additional detection system 300 with the signals from the sensors 240. For example, the capacitive sensors 240 can be used as secondary, or verification sensors that affirm indications from the additional detection system 300. In one example, the additional detection system 300 can include an IMU in a wearable device on the user's person, and the controller 160 is configured to affirm position, orientation and/or motion detected by the IMU (e.g., look left/right or lean forward/backward) with user position, orientation and/or motion as detected by the capacitive sensors 240 (e.g., as indicated by sensors 240 in distinct zones 290). In particular implementations, the controller 160 is configured to take action based on the user movement as detected by the additional detection system 300 only if the signals from the sensors 240 confirm that user movement.

In additional implementations, the controller 160 is configured to use data indicative of position, orientation and/or motion detected by the capacitive sensors 340 to aid in correcting for uncertainty in measurement by one or more additional detection system(s) 300, e.g., in correcting for IMU drift, occlusion in a camera system, and/or noise interference in a microphone system. In certain implementations, e.g., where the additional detection system 300 is part of a wearable device (e.g., an IMU in a wearable device such as a smart device or wearable audio device), the data from sensors 240 can be beneficially used by the controller 160 to verify user position, orientation and/or movement, as well as resetting position and/or orientation for one or more additional detection systems 300. In particular cases, the controller 160 uses data from sensors 240 to maintain steady positional information while one or more additional detection systems 300 have periods of uncertainty.

In contrast to conventional systems and approaches, various aspects of the disclosure enable detection of user proximity in a seated environment. In certain cases, this proximity detection can be used to control various functions in the environment and/or enable gesture-based, proximity-based or other movement-based commands. Additionally, the systems and approaches disclosed according to various implementations can be configured to aid in driver/user monitoring in vehicles (e.g., eye tracking) to enhance safety. For example, systems and approaches disclosed herein can aid in monitoring user alertness by providing reliable detection of user body and/or head position.

Certain components in the disclosed systems may not be depicted, but are understood to enable various additional functions. For example, systems can include additional electronics including but not limited to power source(s), processors, memory, communications components such as transmitters/receivers, network connection equipment (including but not limited to: Wi-Fi, Bluetooth, cellular or near field communications (NFC) equipment) and location-identification components (e.g., GPS systems). Additionally, systems disclosed herein can include one or more interfaces allowing user interaction that includes one or more conventional inputs, such as haptic inputs including a dial, button, touch screen, etc. The interface can also include a voice command interface, such that the user can make adjustments using voice commands. The interface can also include a gesture-based interface, such that the user can make adjustments with gestures (e.g., hand wave, nodding, etc.).

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

Additionally, actions associated with implementing all or part of the functions described herein can be performed by one or more networked computing devices. Networked computing devices can be connected over a network, e.g., one or more wired and/or wireless networks such as a local area network (LAN), wide area network (WAN), personal area network (PAN), Internet-connected devices and/or networks and/or a cloud-based computing (e.g., cloud-based servers).

In various implementations, components described as being "coupled" to one another can be joined along one or more interfaces. In some implementations, these interfaces can include junctions between distinct components, and in other cases, these interfaces can include a solidly and/or integrally formed interconnection. That is, in some cases, components that are "coupled" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" can be linked via conventional hard-wired and/or wireless means such that these electronic components can communicate data with one another. Additionally, sub-components within a given component can be considered to be linked via conventional pathways, which may not necessarily be illustrated.

A number of implementations have been described. Nevertheless, it will be understood that additional modifications may be made without departing from the scope of the inventive concepts described herein, and, accordingly, other implementations are within the scope of the following claims.

We claim:

1. An automobile seat, comprising:
a core section;
a cover over at least a portion of the core section, the cover comprising a set of capacitive sensors across a front of the seat;
a processor for processing signals from the set of capacitive sensors to detect a proximity of a user, wherein the set of capacitive sensors are arranged in a matrix across the front of the seat; and
a controller coupled with the processor, wherein the controller enables gesture-based control of functions in the automobile, wherein gesture-based control of functions in the automobile are based on the detected proximity of the user to the set of capacitive sensors, wherein the functions in the automobile comprise at least one of: an audio playback setting in the automobile or microphone functionality in the automobile.

2. The automobile seat of claim 1, wherein the matrix of capacitive sensors are located in at least one of: a headrest portion of the seat or in a backrest portion of the seat.

3. The automobile seat of claim 1, wherein the matrix of capacitive sensors are distributed on both sides of a vertical centerline of the front of the seat, and wherein the processor is configured to detect side-to-side movement of the user based on signals from the matrix of capacitive sensors or a relative position of the user to the matrix of capacitive sensors,
wherein the matrix of capacitive sensors are distributed on both sides of a horizontal centerline of the front of the seat, and wherein the processor is configured to detect vertical movement of the user based on signals from the matrix of capacitive sensors or a relative position of the user to the matrix of capacitive sensors.

4. The automobile seat of claim 1, wherein the matrix of capacitive sensors comprise at least four zones, with at least two zones located on each side of a vertical centerline of the seat, wherein zones on a same side of the vertical centerline are configured to detect vertical movement of the user and zones on a same side of the horizontal centerline are configured to detect horizontal movement of the user.

5. The automobile seat of claim 4, wherein the controller enables gesture-based control of audio playback settings based on changes in detected proximity of the user to the set of capacitive sensors, wherein the controller is configured to determine a gesture as an intentional control input to the capacitive sensors, wherein the set of capacitive sensors is configured to detect both a head nod gesture by the user and a head shake gesture by the user.

6. The automobile seat of claim 4, wherein the controller enables gesture-based control of the microphone functionality in the automobile by:
receiving an indicator from the set of capacitive sensors that a head position of the user has changed; and
adjusting the microphone functionality to enhance voice pickup from a direction aligned with the head position of the user after the change in head position.

7. The automobile seat of claim 4, wherein the matrix of capacitive sensors comprise at least six zones, with at least three zones located on each side of the vertical centerline.

8. The automobile seat of claim 4, wherein the set of capacitive sensors is configured to detect at least one of: a leaning movement of the user, side-to-side movement of the user, shifting movement of the user, or movement between a seated position and an unseated position.

9. The automobile seat of claim 1, wherein the controller is configured to control output of at least one audio prompt requesting gesture-based user feedback that is detectable with a change in a head position of the user, and wherein the controller is configured to process the gesture-based user feedback as a change in the head position of the user only for a designated period following output of the at least one audio prompt.

10. The automobile seat of claim 1, wherein the controller is further configured to process signals from an additional detection system, and wherein the controller is configured to perform at least one of:
verifying the signals from the additional detection system with the signals from the set of capacitive sensors, or
verifying at least one of a position or orientation of the user as detected by the additional detection system with the signals from the set of capacitive sensors.

11. The automobile seat of claim 1, wherein the core comprises a skeletal support structure, the cover comprises a fabric, and the set of capacitive sensors are embedded within the fabric or woven into the fabric.

12. A system comprising:
an automobile seat comprising:
a core section;
a cover over at least a portion of the core section, the cover comprising a set of capacitive sensors across a front of the seat for detecting a head position of a user, wherein the set of capacitive sensors are arranged in a matrix across the front of the automobile seat;
a processor coupled with the set of capacitive sensors for detecting a proximity of a user; and a controller coupled with the processor, wherein the controller enables gesture-based control of functions in the automobile, wherein gesture-based control of functions in the automobile are based on the detected proximity of the user to the set of capacitive sensors, wherein the functions in the automobile comprise at least one of: an audio playback setting in the automobile or microphone functionality in the automobile.

13. The system of claim 12, wherein the controller is configured to control at least one of the audio playback setting in the automobile or the microphone functionality in the automobile based on the detected proximity of the user by:
initiating output of at least one audio prompt via the transducer, the at least one audio prompt requesting user feedback that is detectable with a change in the proximity of the user to at least one of the set of capacitive sensors; and
processing the user feedback as a change in the proximity of the user to the at least one capacitive sensor only for a designated period following output of the at least one audio prompt.

14. The system of claim 12, wherein the matrix of capacitive sensors comprise at least four zones, with at least two zones located on each side of a vertical centerline of the seat, wherein zones on a same side of the vertical centerline are configured to detect vertical movement of the user and zones on a same side of the horizontal centerline are configured to detect horizontal movement of the user wherein the matrix of capacitive sensors is configured to detect both a head nod gesture by the user and a head shake gesture by the user.

15. The automobile seat of claim 1, wherein in controlling the audio playback setting in the automobile the controller is configured to adjust a center image of the audio output from the set of transducers in response to detecting that the user moves within the seat.

16. The automobile seat of claim 15, wherein the adjusting of the center image of the audio output maintains a stable center image for the user during movement by the user.

17. An automobile seat, comprising:
a core section;
a cover over at least a portion of the core section, the cover comprising a set of capacitive sensors across a front of the seat;
a processor for processing signals from the set of capacitive sensors to detect a proximity of a user; and
a controller coupled with the processor, wherein the controller is configured to control functions in the automobile based on the detected proximity of the user, wherein the functions in the automobile microphone functionality in the automobile,
wherein the controller is configured to control the microphone functionality in the automobile by:
receiving an indicator that a head position of the user has changed; and
adjusting the microphone functionality to enhance voice pickup from a direction aligned with the head position of the user after the change in head position.

18. The automobile seat of claim 17, wherein the controller is configured to adjust beamforming coefficients to enhance microphone pickup based on positional estimates or indicators from the set of capacitive sensors.

19. The automobile seat of claim 17, wherein the controller is configured to enable voice commands in response to receiving an indicator from the set of capacitive sensors that the user is looking forward and disable voice commands in response to receiving an indicator from the set of capacitive sensors that the user is looking down or to the side.

20. The automobile seat of claim 1, further comprising a set of transducers for providing an audio output to the user, wherein controlling the audio playback setting comprises adjusting audio signal filters to the set of transducers based on detected movement by the user as indicated by the set of capacitive sensors.

* * * * *